(12) United States Patent
Morningstar

(10) Patent No.: US 7,244,227 B2
(45) Date of Patent: Jul. 17, 2007

(54) IMPLANTABLE PENILE PROSTHESIS PUMP

(75) Inventor: Randy L. Morningstar, Brooklyn Park, MN (US)

(73) Assignee: AMS Research Corporation, Minnetonka, MN (US)

( * ) Notice: Subject to any disclaimer, the term of this patent is extended or adjusted under 35 U.S.C. 154(b) by 451 days.

(21) Appl. No.: 10/797,470

(22) Filed: Mar. 10, 2004

(65) Prior Publication Data

US 2004/0220447 A1    Nov. 4, 2004

Related U.S. Application Data

(60) Provisional application No. 60/508,123, filed on Oct. 2, 2003, provisional application No. 60/453,684, filed on Mar. 10, 2003.

(51) Int. Cl.
*A61F 5/00* (2006.01)
(52) U.S. Cl. ........................................................ 600/40
(58) Field of Classification Search ............ 600/38–41, 600/29–32; 623/11.11; 128/843
See application file for complete search history.

(56) References Cited

U.S. PATENT DOCUMENTS

| | | |
|---|---|---|
| 3,954,102 A | 5/1976 | Buuck |
| 4,222,377 A | 9/1980 | Burton |
| 4,224,934 A | 9/1980 | Scott et al. |
| 4,235,227 A | 11/1980 | Yamanaka |
| 4,267,829 A | 5/1981 | Burton et al. |
| 4,383,525 A | 5/1983 | Scott et al. |
| 4,407,278 A | 10/1983 | Burton et al. |
| 4,412,530 A | 11/1983 | Burton |
| 4,441,491 A | 4/1984 | Evans, Sr. |
| 4,566,446 A | 1/1986 | Fogarty |

(Continued)

FOREIGN PATENT DOCUMENTS

DE    25 37 506 A1    3/1977

(Continued)

OTHER PUBLICATIONS

Gregory, John G. et al., The Inflatable Penile Prosthesis: Failure of the Rear Tip Extender in Reducing the Incidence of Cylinder Leakage, The Journal of Urology, vol. 131, pp. 668-669 (Apr. 1984).

(Continued)

*Primary Examiner*—John P. Lacyk
(74) *Attorney, Agent, or Firm*—Jose' W. Jimenez; Kimberly K. Baxter

(57) ABSTRACT

A penile prosthesis is provided, which includes at least one cylinder, a reservoir, and a pump including a pump housing, at least one reservoir channel fluidly coupling the pump housing to the reservoir, at least one cylinder tube fluidly connecting the pump housing to the cylinders, and a fluid passageway fluidly coupled to the cylinder tube and a transfer chamber. The pump further includes a first poppet and a second poppet, each of which is biased toward its respective valve seat within the fluid passageway. A bypass chamber is fluidly connected to the fluid passageway by a bypass input channel and a bypass output channel. The bypass chamber comprises a bypass check valve biased toward a closed position. The pump also includes a pump bulb fluidly connected to the fluid passageway between the bypass input channel and bypass output channel along the length of the fluid passageway.

19 Claims, 10 Drawing Sheets

U.S. PATENT DOCUMENTS

| | | | |
|---|---|---|---|
| 4,572,168 A | 2/1986 | Fischell | |
| 4,590,927 A | 5/1986 | Porter et al. | |
| 4,596,242 A | 6/1986 | Fischell | |
| 4,602,625 A | 7/1986 | Yachia et al. | |
| 4,651,721 A | 3/1987 | Mikulich et al. | |
| 4,653,485 A | 3/1987 | Fischell | |
| 4,682,583 A | 7/1987 | Burton et al. | |
| 4,718,410 A | 1/1988 | Hakky | |
| 4,782,826 A | 11/1988 | Fogarty | |
| 4,807,608 A | 2/1989 | Levius | |
| 4,895,139 A | 1/1990 | Hauschild et al. | |
| 5,010,882 A | 4/1991 | Polyak et al. | |
| 5,048,510 A | 9/1991 | Hauschild et al. | |
| 5,062,417 A | 11/1991 | Cowen | |
| 5,112,295 A | 5/1992 | Zinner et al. | |
| 5,114,398 A | 5/1992 | Trick et al. | |
| 5,141,509 A | 8/1992 | Burton et al. | |
| 5,167,611 A | 12/1992 | Cowan | |
| 5,171,272 A | 12/1992 | Levius | |
| 5,250,020 A | 10/1993 | Bley | |
| 5,263,981 A | 11/1993 | Polyak et al. | |
| 5,344,388 A | 9/1994 | Maxwell et al. | |
| 5,704,895 A | 1/1998 | Scott et al. | |
| 5,851,176 A | 12/1998 | Willard | |
| 6,171,233 B1 | 1/2001 | Willard | |
| 6,443,887 B1 | 9/2002 | Derus et al. | |
| 6,723,042 B2 | 4/2004 | Almli et al. | |
| 2002/0033564 A1 | 3/2002 | Koyfman | |

FOREIGN PATENT DOCUMENTS

| | | |
|---|---|---|
| EP | 0 397 500 A2 | 11/1990 |
| WO | WO 92/03107 A | 3/1992 |

OTHER PUBLICATIONS

Hellstrom, WJG, Three-Piece Inflatable Penile Prosthesis Components (Surgical Pearls on Reservoirs, Pumps, and Rear-Tip Extenders), Int'l J of Impotence Research, vol. 15, Suppl. 5, pp. S136-S138 (2003).

Joseph, David et al., Bilateral Dislocation of Rear Tip Extenders From the Inflatable Penile Prosthesis, The Journal of Urology, vol. 128, pp. 1317-1318 (Dec. 1982).

Kim, Sae-Chul, M.D., Mechanical Reliability of AMS Hydraulic Penile Prosthesis, Journal of Korean Medical Science, vol. 10, No. 6, pp. 422-425 (Dec. 1995).

Levine, Laurence A. et al., Mechanical Reliability and Safety of, and Patient Satisfaction With the Ambicor Inflatable Penile Prosthesis: Results of a 2 Center Study, The Journal of Urology, vol. 166, pp. 932-937 (Sep. 2001).

Malloy, Terrance R. et al., Improved Mechanical Survival With Revised Model Inflatable Penile Prosthesis Using Rear-Tip Extenders, The Journal of Urology, vol. 128, pp. 489-491 (Sep. 1982).

Montague, Drogo K., Experience With Semirigid Rod and Inflatable Penile Prosthesis, The Journal of Urology, vol. 129, pp. 967-968 (May 1983).

Mooreville, Michael et al., Implantation of Inflatable Penile Prosthesis in Patients With Severe Corporeal Fibrosis: Introduction of a New Penile Cavernotome, The Journal of Urology, vol. 162, pp. 2054-2057 (Dec. 1999).

Mulcahy, John J., Distal Corporoplasty for Lateral Extrusion of Penile Cylinders, The Journal of Urology, vol. 161, pp. 193-195 (Jan. 1999).

Parulkar, B.G. et al., Revision Surgery for Penile Implant, Int. J. Impotence Res., vol. 6, pp. 17-23 (1994).

Randrup, Eduardo R., M.D., Penile Implant Surgery: Rear Tip Extender That Stays Behind, Urology, vol. XXXIX, No. 1, pp. 667-669 (Jan. 1992).

Stein, Avi et al., Malleable Penile Prosthesis Removal Leaving Behind the Rear Tip Extenders; A Clinical Presentation, Urol. Int., 50, pp. 119-120 (1993).

AMS700™ *Inflatable Penile Prosthesis Product Line, Inservice Script* brochure, American Medical Systems (1992).

*Ultrex/Ultrex Plus* brochure, American Medical Systems, Inc. (1998).

Description of Ultrex Fabric and Yarns (Mar. 30, 2001).

Mentor Alpha I® Inflatable Penile Prosthesis, Surgical Protocol, 15 pages (1998).

Mentor Urology Products, 20 pages (May 1998).

Mentor Alpha I® , The Results are In, 14 pages (Apr. 1997).

Mentor Alpha I® Narrow Base, Simplifying Penile Implant Surgery by Making Difficult Cases More Manageable, 2 pages (Oct. 1996).

Mentor® Acu-Form® Penile Prosthesis, 2 pages (Aug. 1997).

Mentor® Acu-Form® Penile Prosthesis, Malleable Penile Prosthesis, Surgical Protocol, 8 pages (Sep. 1997).

Mulcahy, John J., Another Look at the Role of Penile Prosthesis in the Management of Impotence, pp. 169-185 (1997).

IMPLANTABLE PENILE PROSTHESIS PUMP

REFERENCE TO RELATED APPLICATIONS

This application claims the benefit of U.S. Provisional applications having Ser. No. 60/453,684, filed Mar. 10, 2003, entitled "IMPROVED IMPLANTABLE PUMP," and Ser. No. 60/508,123, filed Oct. 2, 2003, entitled "IMPLANTABLE PENILE PROSTHESIS HAVING A PRESSURIZED RESERVOIR," which applications are incorporated herein by reference in their entirety.

TECHNICAL FIELD

The present invention relates to systems for treating erectile dysfunction and other urological disorders. In particular, the invention relates to inflatable implantable penile prostheses.

BACKGROUND OF THE INVENTION

One common treatment for male erectile dysfunction includes the implantation of a penile implant device. One type of penile implant device includes a pair of cylindrical prostheses that are implanted into the corpus cavernosae of the penis. Typically, the cylindrical prostheses or cylinders are inflatable and are connected to a fluid-filled reservoir through a pump and valve assembly. With one such type of system, one tube extends from each of the two cylindrical prostheses and connects to the pump, and one tube connects the pump to the reservoir. The pump is typically surgically implanted into the scrotum of the patient and the reservoir is implanted in the abdomen, with the tubes fluidly connecting the components. To activate the penile implant device, the patient actuates the pump using one of a variety of methods that cause fluid to be transferred from the reservoir through the pump and into the cylindrical prostheses. This results in the inflation of the prostheses and produces rigidity for a normal erection. Then, when the patient desires to deflate the prostheses, a valve assembly within the pump is actuated in a manner such that the fluid in the prostheses is released back into the reservoir. This deflation returns the penis to a flaccid state.

In three-piece systems such as those described above, the reservoir can sometimes be unintentionally compressed by bending or other pressure in the abdomen, which can lead to an inadvertent and undesirable spontaneous inflation of the cylinders. This can occur because many pump designs are not intended to prevent movement of fluid from the reservoir to the cylinders when the pump is subjected to pressurized fluid from a compressed reservoir. For one example, a pump that includes various poppets, springs, and valve seats can provide for fluid-tight seals for prevention of certain fluid movement under normal reservoir pressures. However, these same fluid-tight seals may be broken or opened when subjected to increased external pressure from the reservoir, thereby allowing fluid to move to and inflate the cylinders. This cylinder inflation can be embarrassing and uncomfortable for the user.

With a three-piece system, the implantation of the three distinct parts of the system (i.e., reservoir, pump, and cylinders) in different parts of the body is typically more invasive to the patient than a system that requires accessing fewer areas of the body. Another system that may be used that typically requires less invasive surgical access can be referred to as a two-piece system. A two-piece system typically differs from a three-piece system in that it does not include a reservoir that is separate from the pump. One such type of system is described, for example, in U.S. Pat. Nos. 4,651,721; 4,895,139; 5,010,882; 5,048,510; and 5,263,981, the entire contents of which are incorporated herein by reference. In these types of systems, the pump itself stores the fluid of the system, thereby also functioning as a reservoir. The pump of this type of system is typically implanted in the scrotum and directly connected to cylinders implanted in the corpus cavernosae of the penis. These systems often involve steps such as manipulating a pump body to activate the pump, then repeatedly squeezing and releasing the pump to transfer fluid to the cylinders. The pump can be squeezed as many times as necessary to achieve the desired firmness of the cylinders. Depending on the system, this can take a significant period of time and may require more repetitive squeezing and releasing cycles than is desirable or convenient for the user.

With both two-piece and three-piece systems, due to the positioning of the pieces of each system relative to each other and the type of pumping mechanism provided with the system, some systems require relatively significant manipulation by the user to transfer fluid to and from the cylindrical prostheses. Such manipulation may be either time-consuming or difficult, particularly for users who have problems with dexterity or complicated instructions. Thus, it is desirable to provide an inflatable prosthetic penile device or system that is easy to activate for cylinder inflation and deflation, and that minimizes or eliminates the chances of spontaneous cylinder inflation.

SUMMARY OF THE INVENTION

The present invention provides certain advantages over other known two-piece and three-piece implantable and inflatable penile prostheses systems. With regard to the two-piece system of the present invention, the use of a pressurized reservoir as an energy-storing device or component aids in providing significant fluid transfer to the cylinders with a single type of motion. That is, the motion that is used to activate the pump is the same motion that is performed to inflate the cylinders. This system thus requires relatively less complicated manipulation to achieve inflation of the cylinders than other commercially available systems. Additionally, because there is not a separate reservoir to implant in the abdomen, the implantation procedure would typically be less complicated than for a system with a separate reservoir. In addition, because there is no reservoir in the abdomen, the chance of reservoir compression and corresponding spontaneous inflation of cylinders is decreased.

In one aspect of the invention a penile prosthesis is provided, which includes at least one cylinder, a reservoir, and a pump for transferring fluid between the reservoir and the at least one cylinder. The pump includes a pump housing, at least one reservoir channel fluidly coupling the pump housing to the reservoir, at least one cylinder tube fluidly connecting the pump housing to the cylinders, and a fluid passageway fluidly coupled to the cylinder tube and a transfer chamber. The transfer chamber is fluidly coupled to the reservoir channel. The pump further includes a first poppet biased toward a first valve seat within the fluid passageway, a second poppet biased toward a second valve seat and generally in alignment with the first poppet within the fluid passageway, and a bypass chamber. The bypass chamber is fluidly connected by a bypass input channel to the fluid passageway at a first location and fluidly connected by a bypass output channel to the fluid passageway at a second location. The bypass chamber comprises a bypass check valve biased toward a closed position. The pump also includes a pump bulb fluidly connected to the fluid passageway between the bypass input channel and bypass output channel along the length of the fluid passageway. In another aspect of the invention, the pump is provided for fluid connection to at least one cylinder.

The prosthesis of the present invention may further be defined by a first poppet having an elongated body with an extending face seal portion, and wherein the fluid passageway comprises a flange extending toward the interior of the fluid passageway for engagement with the face seal portion of the first poppet when the first poppet is displaced by a sufficient distance from the first valve seat. The fluid passageway preferably further comprises a lip seal portion that extends generally from the second poppet toward the first poppet, wherein the first poppet is slideably moveable into contact with the lip seal to prevent fluid from moving between the fluid passageway and the pump bulb. The lip seal provides selective sealing with the first poppet to prevent and allow the movement of fluid during particular modes of operation.

In one mode of operation, when the face seal portion of the first poppet is seated against the first valve seat, the lip seal portion is spaced from the first poppet, and the pump bulb is compressible for forcing enough fluid under pressure from the pump bulb into the fluid passageway to unseat the second poppet from the second valve seat and allow fluid to move past the second poppet and enter the at least one cylinder tube. In addition, when the lip seal portion is in contact with the first poppet, the pump bulb is expandable to place the fluid passageway and transfer chamber under negative pressure to thereby unseat the face seal portion of the first poppet from the first valve seat against the bias of a first poppet spring and draw fluid into the pump bulb. The pump also preferably has a deflation mode in which compression of a portion of the pump body moves the first poppet into sealing contact with both the lip seal portion and the second poppet to unseat the second poppet from the second valve seat to provide a gap for pressurized fluid to flow from the at least one cylinder, past the second poppet, and into the bypass chamber through the bypass input channel. In another mode, which may be referred to as the auto-inflation resistance mode, the first poppet remains in contact with the second poppet and the second poppet remains unseated from the second valve seat, even when the pump body is not under compression.

In accordance with the invention, the reservoir comprises an outer reservoir membrane surrounding at least a portion of an internal reservoir chamber, wherein the reservoir chamber can expand from a first internal volume to a second internal volume that is larger than the first internal volume by the addition of pressurized fluid. Further, in one aspect of the invention, the pump housing comprises a lower face surface, wherein the reservoir chamber is defined by the reservoir membrane and at least a portion of the lower face surface of the pump housing. The lower face surface is preferably not deformable by the pressure of fluid being held within the reservoir chamber. Advantageously, the reservoir can function as an energy-storing device when a volume of pressurized fluid in the reservoir chamber forces expansion of the reservoir membrane.

BRIEF DESCRIPTION OF THE DRAWINGS

The present invention will be further explained with reference to the appended Figures, wherein like structure is referred to by like numerals throughout the several views, and wherein.

DETAILED DESCRIPTION OF THE PREFERRED EMBODIMENTS

Figure 1:
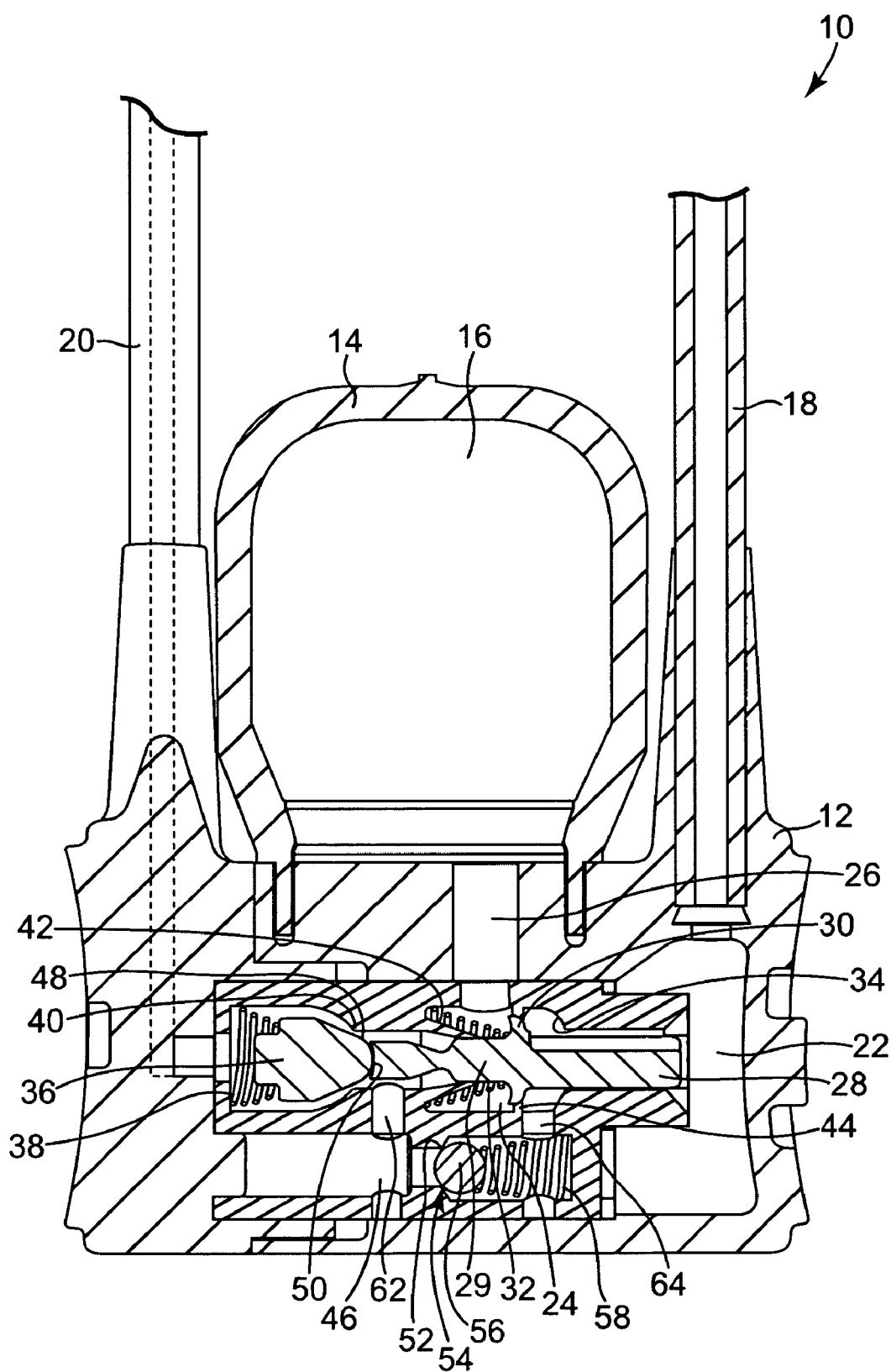
FIG. 1 is a partial cross-sectional front view of one embodiment of a pump assembly of an implantable penile prosthesis device of the present invention, with the pump configured in its auto-inflation resistance mode.

Referring now to the Figures, wherein the components are labeled with like numerals throughout the several Figures and initially to FIG. 1, one preferred configuration of a pump assembly 10 for use in an implantable penile prosthesis system is illustrated. In general, when the penile prosthesis system is implanted into a person, the pump assembly 10 is positioned within the user's scrotum, two inflatable cylinders are positioned within the user's corpus cavernosae and a reservoir is implanted in the user's abdomen. One or more tubes provide fluid communication between the assembly 10 and the cylinders and between the assembly 10 and the reservoir. In this embodiment, the assembly 10 includes a housing or pump body 12 connected to a pump bulb 14 having an internal pump chamber 16. The pump assembly 10 is connected for fluid communication with at least one inflatable cylinder (not shown) by at least one tube 20, which may be a flexible silicone tube, for example. While only one such tube 20 is visible in FIG. 1, the assembly 10 may include additional tubes 20 for connection to multiple inflatable cylinders. Alternatively, a single tube 20 could be fluidly connected directly to the pump assembly 10 and branch into multiple tubes that extend to each of the cylinders at some distance from the pump assembly. Each tube 20 is preferably relatively flexible for comfort and conformability within a patient, and may have a constant or varying (e.g., tapered) diameter along its length.

The pump assembly 10 is further connected for fluid communication with at least one fluid-filled reservoir (not shown) by at least one reservoir tube 18. While only one tube 18 is visible in FIG. 1, the assembly 10 may include additional tubes 18 for connection to one or more reservoirs, or a single tube 18 may be fluidly connected to the pump assembly and branch into multiple tubes that connect to one or more reservoirs. In the preferred embodiment, however, a single tube 18 is provided to fluidly connect the pump assembly 10 to a single reservoir, which is typically implanted in the abdomen or some other location in the user's body that is spaced from the pump assembly 10. Each tube 18 is preferably made of a relatively flexible material, such as silicone, and is sufficiently long for connecting the reservoir to the pump body when these components are implanted in their desired locations in the body.

The pump assembly 10 of the present invention is controllable by the user to move fluid to and from the inflatable cylinders, as desired. Importantly, the pump assembly 10 is designed to eliminate or reduce the possibility of the cylinders becoming inflated unintentionally, such as by compression of the reservoir by the user during an ordinary action such as bending over or otherwise providing increased pressure to the abdomen or other area where the reservoir is implanted. In addition, when the cylinders are at least partially inflated, the pump assembly 10 preferably maintains fluid pressure in the cylinders to maintain them in their inflated or semi-inflated state until the user desires to deflate the cylinders. Thus, the pump assembly 10 provides a controllable device that is easily manipulated by the user to inflate and deflate the cylinders, as desired.

The pump body 12 is preferably a generally flexible device that includes a number of components to provide the desired movement of fluid through its internal chambers. More specifically, one end of the reservoir tube 18 is fluidly connected to a transfer chamber 22 within the pump body 12. Transfer chamber 22 can also fluidly communicate with one end of transfer tube 20 through a connecting fluid passageway 24. The fluid passageway 24 is further connected to the internal pump chamber 16 of pump bulb 14 by a connecting channel 26, where the various fluidic connections can be initiated and terminated with the operation of the pump assembly 10, as described below. As shown, fluid passageway 24 is a generally elongated chamber that extends across a portion of the width of the pump body 12 and provides a passageway through which fluid can flow between the components of the pump assembly 10, such as the reservoir, pump bulb 14, a fluid bypass chamber 46, and the cylinders.

Fluid passageway 24 includes within its internal area a check valve system that generally includes a suction poppet 28 and a poppet 36. Suction poppet 28 and poppet 36 are preferably aligned with each other along the length of the passageway 24, with both poppets preferably being centrally positioned within the passageway 24. The suction poppet 28 has a generally elongated shape including several contours for contact and sealing with various components of the system during its operation. In particular, suction poppet 28 includes an elongated body 29 that is preferably generally cylindrical, although it can take any number of shapes that fit within the internal chamber of the fluid passageway 24 to provide contact with its surfaces and control the movement of fluid. The suction poppet 28 further includes a face seal portion 30 that is preferably a ring-like protrusion that extends around the outer perimeter of the elongated body 29. As shown, the face seal portion 30 is positioned near the center of the length of the elongated body 29, although it is possible that the portion 30 is closer to one of the ends of the elongated body 29 than its other end. The face seal portion 30 is shaped to abut a suction poppet valve seat 34, which is a contoured surface formed within the passageway 24. The surface of the valve seat 34 that comes into contact with the face seal portion 30 is preferably a generally smooth surface that allows for a fluid tight seal between the face seal portion 30 and valve seat 34, when desired. Suction poppet 28 further includes a suction poppet spring 32 that engages suction poppet 28 and biases suction poppet 28 toward the valve seat 34, or toward the right side of the pump body 12 in this Figure.

Fluid passageway 24 further includes a flange 44 configured generally as a ring-like portion within the passageway 24 that preferably extend passageway 24 around the inner perimeter of the fluid passageway 24. The flange 44 is provided to reduce the inner diameter of the passageway 24 by a sufficient amount that the inner diameter in the area of the flange 44 is smaller than the outer diameter of the face seal portion 30. In this way, the flange 44 can engage with the face seal portion 30 to hold the suction poppet 28 against the bias of the spring 32. The flange 44 preferably has sufficient strength to hold the face seal portion 30 against the bias of the spring 32, but also is flexible enough to allow movement of the face seal portion 30 through or past the flange 44 in either direction (i.e., to the right or left). The flange 44 may be annular and extend around the inner perimeter of the passageway 24, as shown, or may instead have a different shape or configuration that can provide the function of engaging and disengaging sufficiently with the face seal portion 30 in the manner described above. Further, the flange 44 may formed integrally with the passageway 24 or may be formed separately and attached to the interior of the passageway 24, such as with adhesives or the like. Suction poppet spring 32 is preferably has sufficient spring force to provide the desired amount of sealing between the face seal portion 30 and the valve seat 34 when the face seal portion 30 is to the right of the flange 44. The spring 32 should not be so strong, however, that it pushes the suction poppet 28 past the flange 44 toward the transfer chamber 22 when it is instead desired for the face seal portion 30 to be on the opposite side of flange 44.

Fluid passageway 24 also includes within its internal area a poppet valve seat 40 adjacent to the poppet 36. Poppet valve seat 40 is an inner surface area that is shaped to allow only a portion of the poppet 36 to extend past it. That is, the poppet 36 is preferably provided with a generally tapered outer surface that allows it to partially move past or through the poppet valve seat 40 until the outer surface of the poppet 36 contacts the valve seat 40. Thus, as the poppet 36 moves to the right in the figure, the outer surface of the poppet 36 will come into contact with the poppet valve seat 40, thereby providing a fluid tight seal in certain modes of the operation of the pump assembly 10. Poppet 36 is provided with a poppet spring 38 that engages poppet 36 and biases poppet 36 toward poppet valve seat 40. The poppet spring 38 is preferably strong enough to provide a fluid tight seal between the poppet 36 and the poppet valve seat 40; however, the spring 38 is preferably not so strong that the poppet 36 is prevented from being moved to the left under sufficient fluid pressure. Such a movement of the poppet 36 away from the poppet valve seat 40 allows fluid to pass from the fluid passageway 24 into the tube 20 during operation of the pump assembly 10.

The internal area or portion of the fluid passageway 24 further includes a lip seal 42 that extends generally from the area near the poppet 36 toward the suction poppet 28. In one preferred embodiment, the lip seal 42 may be generally conical in shape such that it tapers from a first cross-section in the pump body to a point or edge at its other end. This lip seal 42 is shown in cross-section as a finger-like portion that extends into the fluid passageway 24. It is contemplated, however, that the lip seal 42 has a different configuration or shape for sealing against the surface of the suction poppet 28. Lip seal 42 is preferably configured so that it can contact the outer walls of the suction poppet 28 and provide a fluid tight seal between the lip seal 42 and the suction poppet 28 when the suction poppet is positioned as shown in FIG. 1 (i.e., with the face seal portion 30 out of contact with the valve seat 34 and to the left of the flange 44). Lip seal 42 is preferably further configured to allow smooth movement of the suction poppet 28 into and out of contact with the lip seal 42. However, lip seal 42 will be spaced from the outer walls of the suction poppet 28 when the portion of the suction poppet 28 that is adjacent to the lip seal 42 is smaller in diameter than the area adjacent the lip seal 42. This will occur, for example, when the suction poppet 28 is moved so that the face seal portion 30 is in contact with the valve seat 34, as described below. In this mode, fluid would then be able to move through the fluid passageway 24 and past the lip seal 42.

As illustrated in FIG. 1, the poppet 36 includes a nose portion 48 that is contoured to engage with an end 50 of suction poppet 28. In this way, when the suction poppet 28 is moved away from the valve seat 34 so that the face seal portion 30 is engaged with the flange 44 against the bias of the suction poppet spring 32, the end 50 of suction poppet 28 will push against the nose 48 of the poppet 36 against the bias of poppet spring 38, thereby allowing for a certain fluid flow path. Thus, it is also preferable that the poppet spring 38 and the suction poppet spring 32 are chosen to provide the desired ease of movement of components. That is, undue force should not be required to move the springs and poppets through the various operation modes of the pump assembly 10. In particular, it is required for operation of the pump assembly 10 that the sides of the pump body 12 are compressible to thereby manipulate the position of suction poppet 28 and poppet 36 relative to each other and the pump body 12. In order for this to be possible, it is preferable that suction poppet 28 and poppet 36 are in sufficiently close proximity to the sides of the pump body 12 so that squeezing the pump body 12 with a reasonable amount of force will move the components within the pump body 12 into certain positions.

Pump body 12 further includes a fluid bypass chamber 46 that is connected for fluid communication with the fluid passageway 24 under certain operating conditions or modes of the pump. Fluid bypass chamber 46 includes a ball check valve 54 having a ball 56 and a spring 58. The spring 58 biases the ball 56 within the chamber 46 toward a ball valve seat 52, which is a portion or edges of the chamber 46 that form a diameter that is smaller than the diameter of the ball 56. In this way, a fluid tight seal may be formed between the ball 56 and the ball valve seat 52 when the system is in a state of equilibrium. This seal prevents the undesired movement of fluid through the bypass chamber 46 except under certain operating conditions of the pump assembly 10. As with the other springs used in pump assembly 10, spring 58 should be sufficiently strong to keep the ball 56 in its normal or closed position against the ball valve seat 52 under many operating circumstances. However, the spring 58 should also allow for a predetermined flow of fluid against the bias of the spring 58 to move the ball 56 out of contact with the ball valve seat 52 to allow fluid to flow through the bypass chamber 46. As shown, fluid may move from the fluid passageway 24 into the bypass chamber 46 through a bypass input channel 62, which is positioned to the left of the lip seal 42.

When there is a sufficient volume of pressurized fluid in the chamber 46 to move the ball 56 against the bias of the spring 58, the fluid will be able to move freely from the input channel 62 and through the bypass chamber 46. Fluid may then exit the bypass chamber 46 through a bypass output channel 64 that provides a second fluid connection between the bypass chamber 46 and the fluid passageway 24. The bypass output channel 64 is positioned to the right of the lip seal 42 so that certain operating conditions will provide a fluid path in which fluid passes by the suction poppet 28 and enters the transfer chamber 22. The valve style used in the fluid bypass chamber 52 of FIG. 1 is shown as a ball check valve, but it could instead include any number of designs such as a "duck bill valve", flap, or the like, which react to pressurized fluid in generally the same manner as the ball check valve 54.

FIG. 1 illustrates the pump assembly 10 with its components in a configuration that may be referred to as an auto-inflation resistance mode. In this mode, the cylinders are in a deflated condition and spontaneous inflation of the cylinders will preferably be difficult or impossible due to the positions of the poppets, springs and chambers of the pump assembly 10. No inflation of the cylinders can occur until the pump bulb 14 is manipulated in a specified manner. In this mode, the fluid of the system will typically be contained within reservoir tube 18 and the connected transfer chamber 22, and this fluid cannot travel into the tube 20 and the attached cylinders. In this mode, the suction poppet 28 is being held against the bias of the suction poppet spring 32 by the flange 44 within the fluid passageway 24. The end 50 of suction poppet 28 is engaged with the nose portion 48 of poppet 36, thereby pushing the poppet 36 against the bias of poppet spring 38. The suction poppet 28 is thus positioned so that its outer surface is in contact with the lip seal 42, thereby creating a fluid-tight seal between the suction poppet 28 and the lip seal 42.

In most cases, some portion of the fluid from the reservoir will move into the tube 18 and transfer chamber 22, particularly when the reservoir is under pressure. Any such pressurized fluid in the transfer chamber 22 can move into the fluid passageway 24 and move the suction poppet 28 slightly to the left. This movement of suction poppet 28 allows fluid to flow from the transfer chamber 22 through the gap between the face seal portion 30 and suction poppet valve seat 34. This fluid will then enter the internal pump chamber 16 through the connecting channel 26. Movement of fluid into the pump bulb 14 will stop when the pressure has generally equalized between the pump bulb 14 and the reservoir. The bias of suction poppet spring 32 can then move the face seal portion 30 back into contact with the valve seat 34, thereby limiting or preventing further fluid flow into the pump bulb 14.

Because the lip seal 42 and suction poppet 28 form a fluid tight seal, as described above, no fluid may move past this seal toward the tube 20 and connected cylinders. In addition, fluid moving into the fluid bypass chamber 46 through the bypass output channel 64 will be prevented from moving past the ball check valve 54 by the seal of the ball 56 against the ball valve seat 52. Thus, no fluid will be able to pass into the fluid passageway 24 or the tubes 20 by this path. In this state of equilibrium, fluid will thus be held within the reservoir, the connecting reservoir tube 18, the transfer chamber 22, and the internal pump chamber 16. While there may be small amounts of residual fluid contained in the various portions of the pump assembly, it is understood that the cylinders are preferably in their completely deflated or collapsed condition when the pump is configured in this mode.

Figure 2:
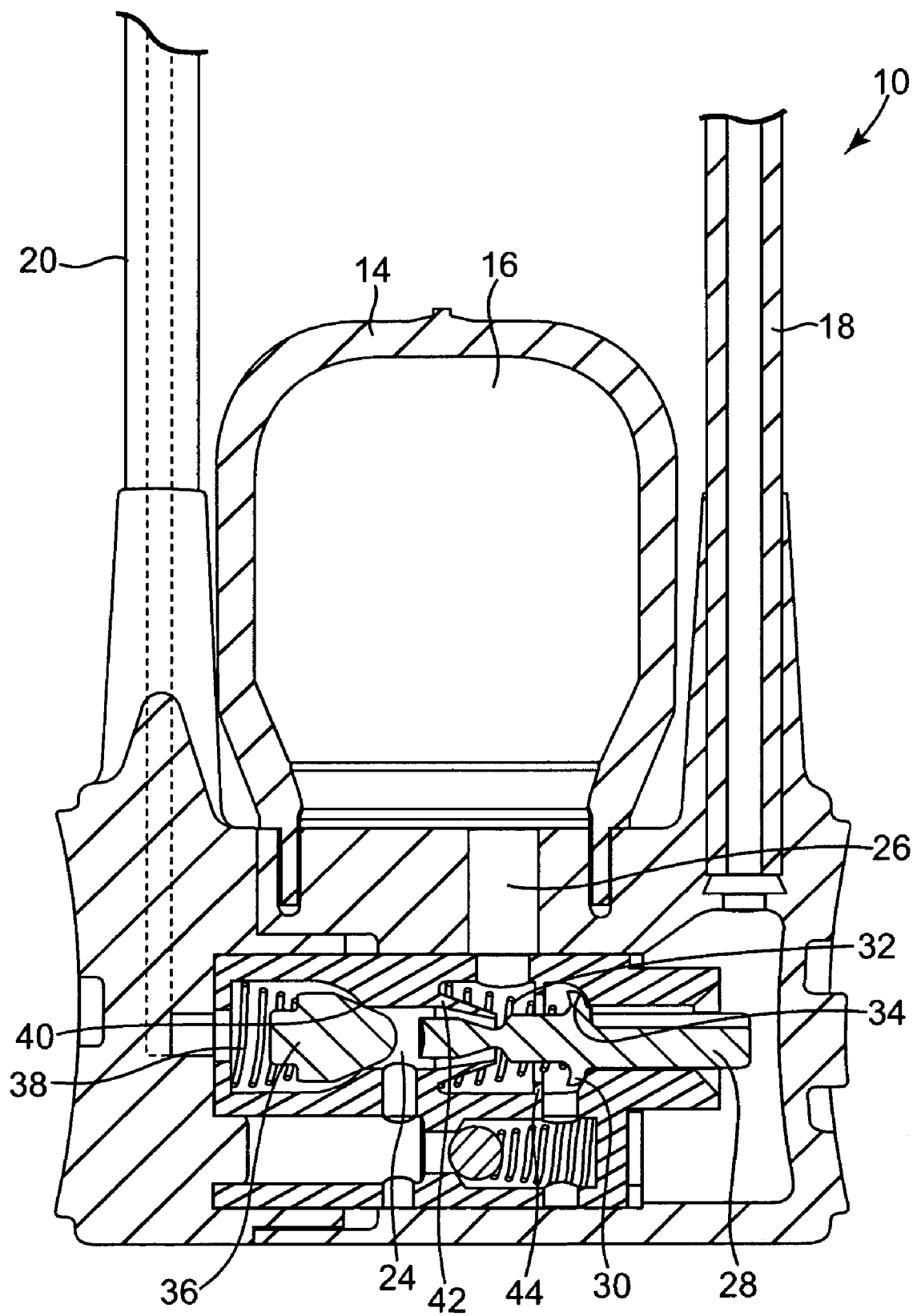
FIG. 2 is a partial cross-sectional front view of a pump assembly of the type illustrated in FIG. 1, with the pump configured in its activation mode.

The activation mode of pump assembly 10 for cylinder inflation is illustrated in FIG. 2. This is the mode in which the user activates the pump assembly to begin the process of cylinder inflation. To activate the pump assembly 10, the pump bulb 14 is squeezed or compressed by the user. This motion forces the fluid contained within pump chamber 16 through connecting channel 26 and into fluid passageway 24 under relatively high fluid pressure. This high pressure fluid forces the face seal portion 30 of suction poppet 28 past the flange 44, which is made of a material that is relatively flexible to allow the face seal portion 30 to move past it, yet sufficiently strong to hold the suction poppet 28 against the bias of its spring 32. The bias of the suction poppet spring 32 will then push the suction poppet 28 and its face seal portion 30 against the suction poppet valve seat 34, thereby providing a fluid tight seal between the face seal 30 and the valve seat 34. Because the portion of the suction poppet 28 adjacent the lip seal 42 is now smaller in diameter than the internal opening provided by the lip seal 42, the lip seal 42 is not in contact with the suction poppet 28 in this mode (i.e., a gap is created between the suction poppet 28 and the lip seal 42). Thus, fluid can move past lip seal 42 and toward the poppet 36. In order for fluid to move past the poppet 36 and into the tube 20, however, the fluid pressure must be high enough to overcome the bias of the poppet spring 38, which is now pushing the poppet 36 in fluid tight contact with the poppet valve seat 40. The amount and pressure of the fluid may or may not be sufficient to cause such a movement of poppet 36 in this pump activation mode.

Figure 3:
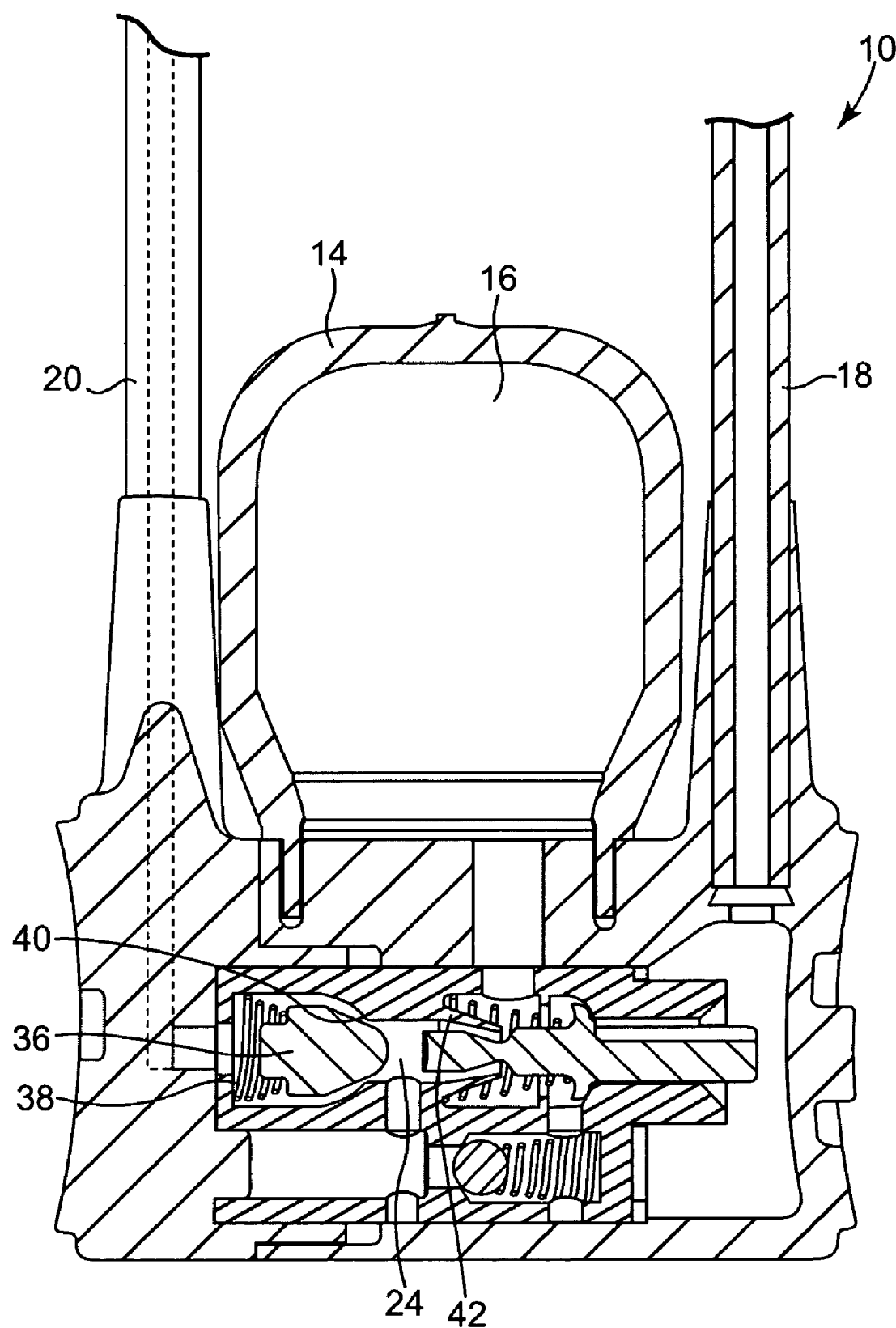
FIG. 3 is a partial cross-sectional front view of a pump assembly of the type illustrated in FIG. 1, with the pump configured in its pumping mode.

FIG. 3 illustrates a situation where the fluid pressure is sufficiently high to overcome the bias of the poppet spring 38, thereby breaking the fluid-tight contact between the poppet 36 and poppet valve seat 40 and providing a gap between these two surfaces. This may be referred to as the pumping mode of pump assembly 10. Fluid may then flow past the lip seal 42 and poppet 36, and then into the tube 20 and the attached inflatable cylinders. In particular, after a first volume of pressurized fluid from the pump bulb is moved past the poppet 36 and into the cylinders (e.g., as described above relative to FIG. 2), the bias of the poppet spring 38 will push the poppet 36 back into contact with the poppet valve seat 40. Pump bulb 14 is preferably selected from a material that is relatively elastic and easy for a user to compress, but should also have sufficient structural integrity that it tends to move back toward its original size or configuration when not subjected to external pressure. That is, when the user releases the bulb 14, it should expand generally to its original shape and size, thereby providing a situation where the pump bulb chamber 16 and fluid passageway 24 are placed under negative pressure. This negative pressure provided by the expansion of the bulb 14 will draw fluid from the reservoir through the reservoir tube 18 and into the pump bulb 14, as illustrated in FIG. 4.

Figure 4:
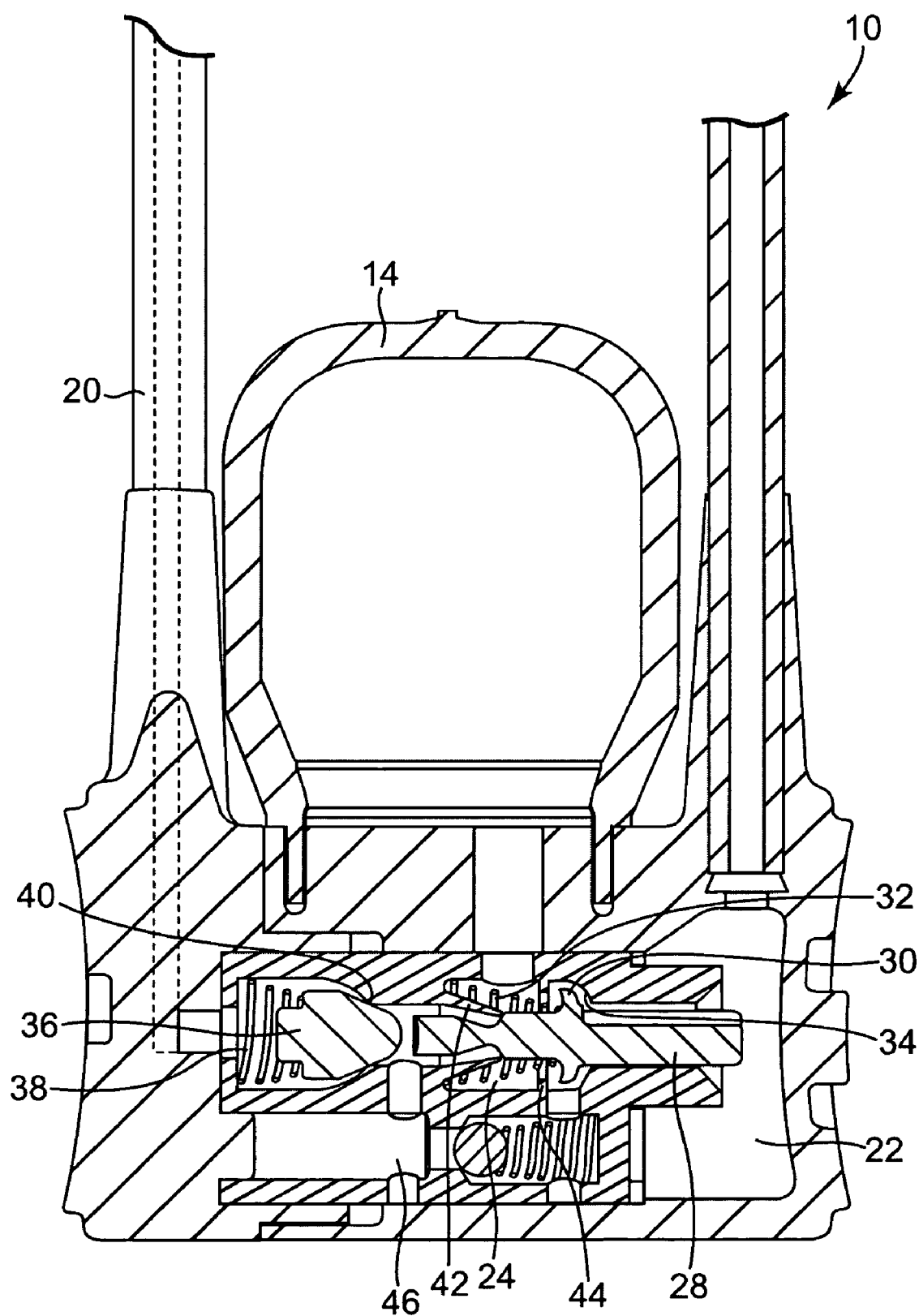
FIG. 4 is a partial cross-sectional front view of a pump assembly of the type illustrated in FIG. 1, with the pump configured in its pump bulb filling mode.

More specifically, FIG. 4 shows the pump assembly 10 in the mode that may be referred to as the pump bulb filling mode. As described above, this mode exemplifies the situation in which the pump bulb 14 is pulling or drawing fluid from the reservoir and through the various chambers of the system. As shown, the negative pressure within the pump bulb 14 and connected chambers moves the suction poppet 28 slightly to the left, thereby breaking the seal between the face seal portion 30 and the suction poppet valve seat 34. Simultaneously, the outer portion of the suction poppet 28 will slide into contact with the lip seal 42 to provide a fluid tight seal between the suction poppet 28 and lip seal 42. Fluid may then flow from the reservoir into the transfer chamber 22, past the face seal portion 30, and into the fluid passageway 24. Because the lip seal 42 and suction poppet 28 are positioned to provide a fluid tight seal, no fluid may move past these surfaces. Rather, any fluid under negative pressure within the fluid passageway 24 will move into the pump bulb 14 until the pump bulb 14 is full and/or there is no longer enough fluid pressure to keep the face seal portion 30 from moving toward the suction poppet valve seat 34. The suction poppet spring 32 then causes the suction poppet 28 to reseat itself against the valve seat 34. At this point, the user may then squeeze or compress the pump bulb 14 to again move fluid from the pump bulb 14 into the tube 20 and inflatable cylinders, as described above relative to FIG. 3.

This sequence of filling the pump bulb 14 under negative pressure and forcing the fluid from the pump bulb 14 under positive pressure may be repeated as many times as necessary to achieve the desired inflation of the cylinders and/or to empty the connected reservoir. Once inflated, the fluid within the cylinders and the tube 20 is under relatively high pressure. While the poppet spring 38 preferably has a sufficiently strong bias to keep the poppet 36 pressed against the poppet valve seat 40, the relatively high pressure fluid in the cylinders and connected chambers also pushes the poppet 36 into contact with the valve seat 40, further strengthening this seal. This seal between the poppet 36 and valve seat 40 is particularly important to keep the cylinders inflated (i.e., to prevent undesirable transfer of fluid from the cylinders into the fluid passageway 24). Because the only path for fluid to move from the tube 20 into the fluid bypass chamber 46 is through the fluid passageway 24, it is likewise not possible for fluid from the cylinders to move into the fluid bypass chamber 46 without first breaking the seal between the poppet 36 and its poppet valve seat 40.

Figure 5:
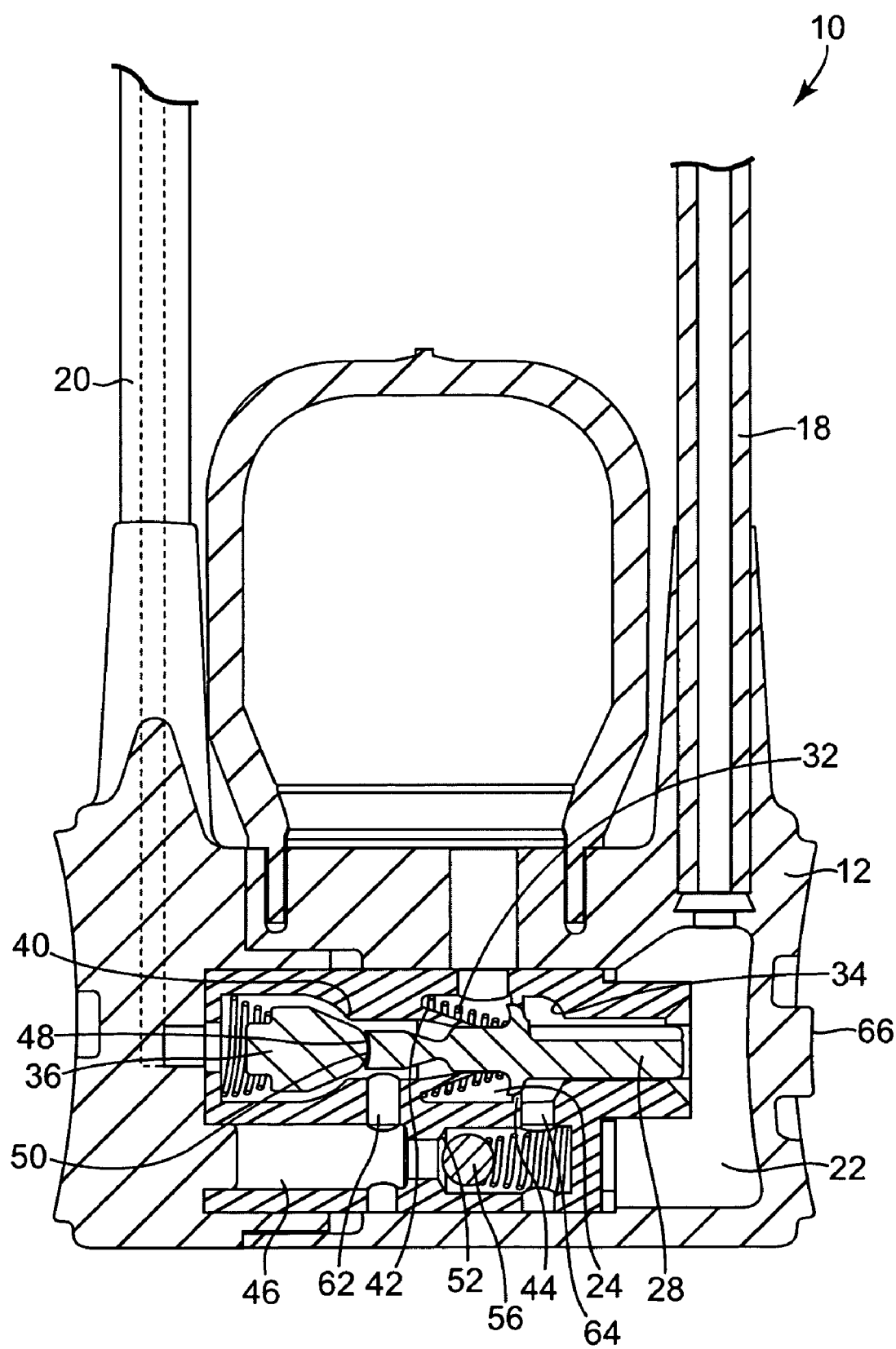
FIG. 5 is a partial cross-sectional front view of a pump assembly of the type illustrated in FIG. 1, with the pump configured in its deflation mode where deflation of the cylinders occurs.

When the user desires to deflate the cylinders, the walls of the pump body 12 will be manually compressed in the general area of the fluid passageway 24, as shown in FIG. 5. In order to assist the user in finding the proper area for compression, the outer surface of the pump body 12 may be provided with raised or otherwise detectable areas for easier determination of proper manipulation locations on the pump body 12. One example of such a detectable area is illustrated as a user pressure pad 66, which is a raised flat area on the side of the pump body 12 that would be detectable by the human fingers. A compressive force on both ends of the pump body 12 forces suction poppet 28 away from the suction poppet valve seat 34 by a sufficient distance that the face seal portion 30 moves to the left past the flange 44. The flange 44 then engages the face seal portion to hold the suction poppet 28 in place against the bias of the suction poppet spring 32. This compression of the pump body 12 simultaneously moves the end 50 of suction poppet 28 into contact with the nose portion 48 of poppet 36, which also breaks the seal between the poppet 36 and the poppet valve seat 40. Further, the pump body compression also causes the suction poppet 28 to be in a position where the lip seal 42 is in contact with the suction poppet 28, which provides a fluid tight seal between these surfaces. Fluid from the cylinders and connecting tube 20 may then flow around the poppet 36, past the poppet valve seat 40, and into the bypass input channel 62. Notably, a single compressive squeeze by the user is sufficient to put the pump assembly 10 in this cylinder deflation mode. In other words, there is no need for the user to continue to hold the pump body 12 in this compressive condition while the cylinder deflation is occurring. Once the fluid enters the bypass input channel 62, it moves directly into the fluid bypass chamber 46, where sufficient fluid pressure can unseat the ball 56 from the ball valve seat 52 and allow fluid to move out of the chamber 46 through the bypass output channel 64 and into the fluid passageway 24. The fluid can then move through the transfer chamber 22 to the tube 18, and then into the reservoir.

Because the fluid within the cylinders before deflation is under relatively high pressure, an initial volume of pressurized fluid will move under pressure from the tube 20 and into the pump body 12 upon compression of the pump body. After this initial volume has been transferred and the fluid has reached an equilibrium pressure, the cylinders may be manually compressed or manipulated to transfer the remainder of the fluid to the reservoir without the need to hold the pump, thereby completely deflating the cylinders. The pump assembly 10 is then configured again in its auto-inflation resistance mode, as described above relative to FIG. 1. The sequence of steps described will be initiated when the user again wishes to inflate the cylinders.

The reservoir is preferably a relatively flexible membrane that is sized to hold a sufficient amount of fluid for proper inflation of a pair of cylinders when desired. In particular, the reservoir membrane is preferably relatively elastic so that the membrane can stretch to hold all of the fluid transferred from the cylinders and can collapse when the fluid is transferred from the reservoir to the cylinders. However, the reservoir membrane does not necessarily need to be elastic. The membrane should also be strong enough to hold fluid under pressure within the reservoir for extended periods of time without the membrane relaxing or otherwise deteriorating and losing pressure.

Figure 6:
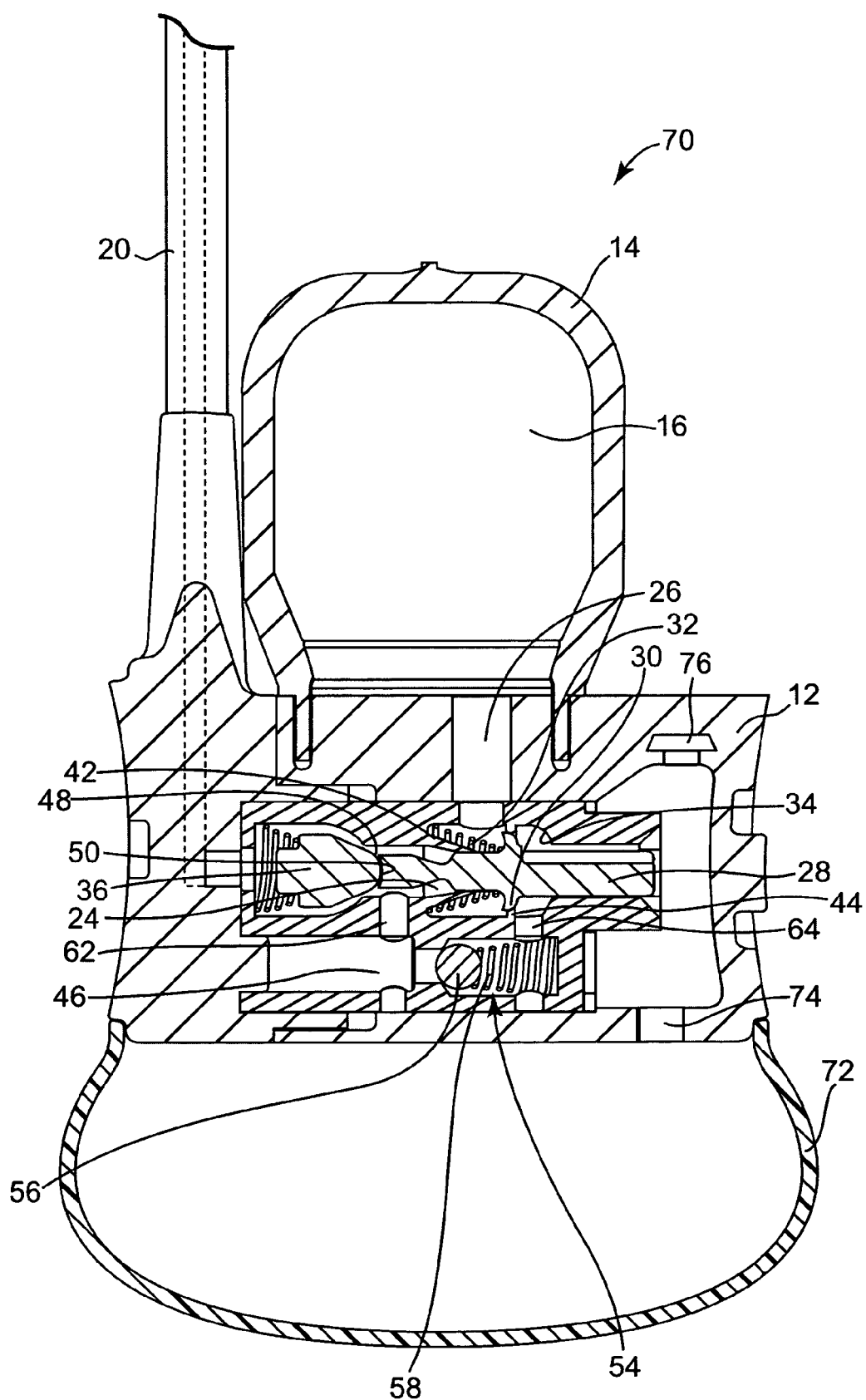
FIG. 6 is a partial cross-sectional front view of another embodiment of a pump assembly of the present invention, with the pump configured in its auto-inflation resistance mode and attached to a reservoir in its charged or filled condition.
Figure 7:
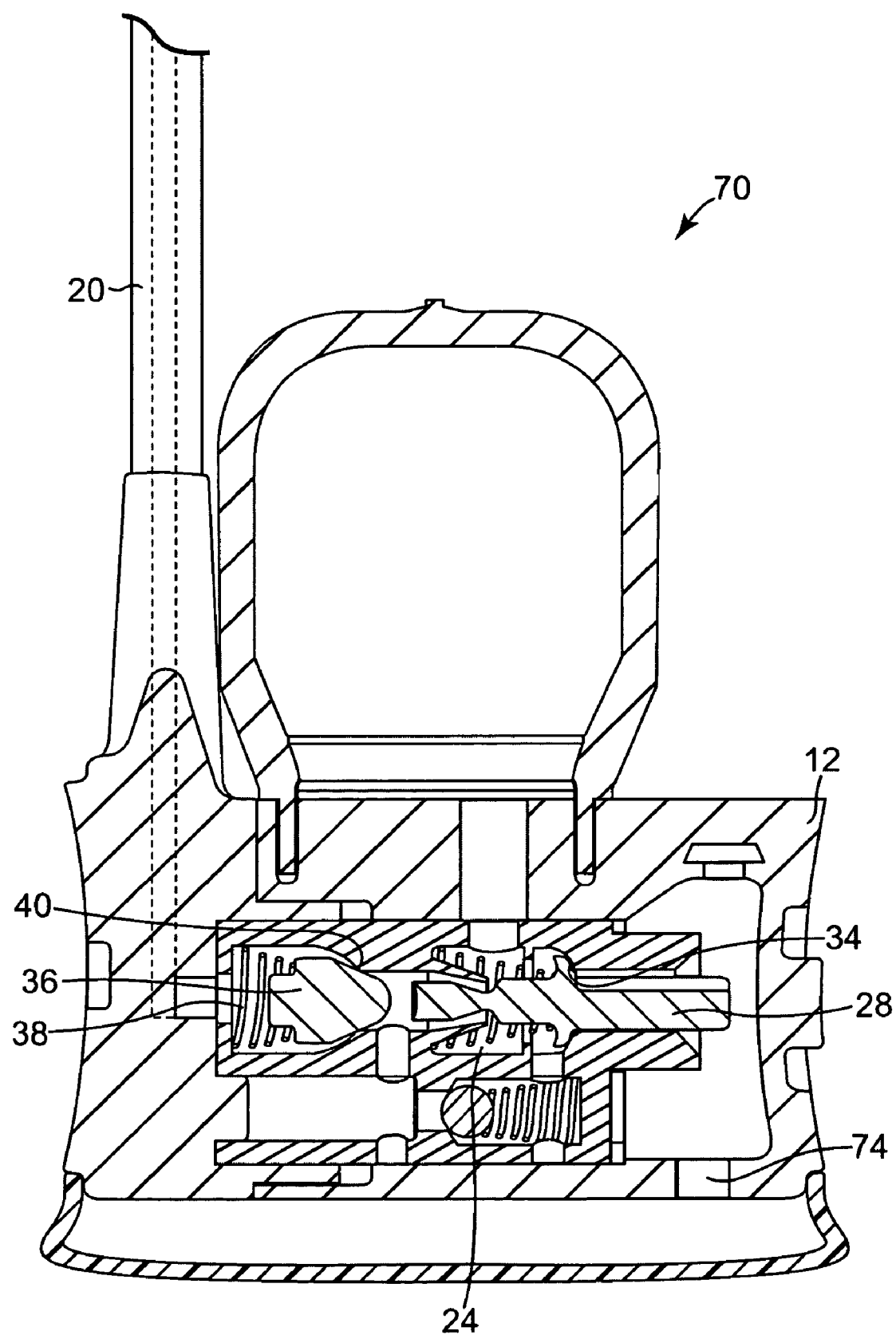
FIG. 7 is a partial cross-sectional front view of the pump assembly of FIG. 6, with the pump configured in its activated mode and attached to a reservoir in its discharged or collapsed condition.

FIGS. 6 and 7 illustrate another embodiment of a pump assembly 70 in accordance with the present invention, which includes many of the same elements as the embodiment described above relative to FIGS. 1 through 5. These elements are referred to with like numerals as those used for the previously described embodiment. In particular, the pump assembly 70 includes a pump body 12 connected to a pump bulb 14 having an internal pump chamber 16. The pump assembly 70 is connected for fluid communication with at least one inflatable cylinder (not shown) by at least one tube 20. The pump body 12 further includes a reservoir 72 which is fluidly connected to the pump body 12 and preferably positioned to be generally on the opposite side of the pump assembly 70 as the pump bulb 14.

The system with which a pump assembly 70 is used may be referred to as a two-piece system since the reservoir 72 is attached directly to the additional tubing between these components. That is, many known prosthesis devices are referred to as three-piece systems, such as the prosthesis device in which the pump assembly 10 described above is used. These three-piece systems typically include a pump assembly placed in the scrotum, a reservoir placed in the abdomen, and two cylinders placed in the corpus cavernosae of the penis. These three components are in fluid communication with each other through connecting tubing. With the two-piece system of the present embodiment, the reservoir 72 and pump assembly 70 provide a single unit for placement within the scrotum, thereby eliminating the need for additional tubing between the pump body 12 and the reservoir 72. Because there is not a separate reservoir to implant in the abdomen, the implantation procedure would typically be less complicated than for a system with a separate reservoir. In addition, because there is no reservoir in the abdomen and due to the auto-inflation resistant design of the pump assembly 70, the chance of spontaneous inflation of cylinders is decreased or eliminated with the present invention.

The reservoir 72 is preferably used as an energy-storing element or device that can provide significant fluid transfer to and from the cylinders with a minimal amount of manipulation of the prosthesis device during inflation and deflation of the cylinders. A number of variables should be considered for selection of the reservoir 72, such as the material from which the reservoir is made, including its flexibility and elasticity, the amount of fluid the reservoir can hold, and other factors. More specifically, the reservoir 72 is preferably a relatively flexible membrane that is sized to hold a sufficient amount of fluid for proper inflation of a pair of cylinders when desired. In particular, the reservoir membrane is preferably relatively elastic so that the membrane can stretch to hold all of the fluid transferred from the cylinders and collapse when the fluid is transferred from the reservoir to the cylinders. The reservoir membrane should also be strong enough to hold fluid under pressure within the reservoir for extended periods of time without the membrane relaxing or otherwise deteriorating and losing pressure.

The pump body 12 includes a reservoir channel 74 that extends from an internal transfer chamber 22 through the thickness of the pump body 12 to terminate at the edge or bottom of the body. The reservoir 72 is connected for fluid communication with the transfer chamber 22 through this reservoir channel 74. The reservoir channel 74 can extend through the pump body 12 at a different location than that shown in the figure, or it is possible that the pump body 12 includes more than one reservoir channel 74 for connection to reservoir 72. However, in order to prevent the reservoir 72 from interfering with any manipulation of the pump body 12 and to provide a relatively compact design for the pump assembly 10, the reservoir 72 is preferably positioned in the general location shown and is connected to the pump body 12 through a single channel. This location of the channel 74 is also advantageous in that it requires only a short reservoir channel 74, which allows for quick transfer of fluid from the reservoir 72 into the transfer chamber 22. The reservoir 72 may be connected to the pump body 12 by any method that provides a fluid-tight seal that does not fail when subjected to relatively high fluid pressure. For example, adhesives may be used to secure the membrane of reservoir 72 to the pump body 12. Further, while the reservoir 72 is shown to be attached to the pump body 12 on opposite ends of the bottom of the pump body 12, the reservoir could instead be attached to the pump body 12 in different locations on the pump body 12, such as on the sides of the pump body or at a location that is offset from the ends of the pump body bottom. Alternatively, the reservoir membrane may be attached to a tube or other structure that extends from the channel 74.

The pump assembly 70 further includes a fluid passageway 24 that extends across the width of the pump body 12, providing a passageway for fluid to flow between the transfer chamber 22, to which it is connected, and the tube 20. Transfer chamber 22 further preferably includes a filling port or valve 76 used for the initial filling and pressurization of the system with fluid, such as saline. However, the particular filling location can be different from that shown, and any particular system may include multiple filling ports or devices, if desired. The fluid passageway 24 further includes a suction poppet 28 and poppet 36 that are both spring biased to seat against their respective valve seats in certain operation modes of the pump. The suction poppet 28 includes a generally elongated body with a face seal portion 30 that extends as a ring-like protrusion from the elongated body around its outer perimeter. The face seal portion 30 can be engaged by a flange 44 that extends into the fluid passageway 24 to hold the suction poppet 28 against the bias of its suction poppet spring 32. When the suction poppet is moved so that the face seal portion 30 is past the flange 44 (i.e., to the right of the flange 44 in this figure), the bias of the suction poppet spring 32 can then press the face seal portion 30 into contact with a suction poppet valve seat 34 to create a fluid-tight seal between these surfaces.

The internal area of the fluid passageway 24 further includes a lip seal 42 that is configured so that it can contact the outer walls of the suction poppet 28 when the portion of the suction poppet 28 that is relatively large in diameter is adjacent the lip seal 42. The lip seal 42 will be spaced from the outer walls of the suction poppet 28, however, when the portion of the suction poppet 28 that is adjacent to the lip seal 42 is smaller in diameter than the area adjacent the lip seal 42. The lip seal 42 may be generally conical in shape so that it tapers to a point or end that can move into and out of contact with the suction poppet 28. The lip seal 42 also preferably slides smoothly into and out of contact with the contoured surfaces of the suction poppet 28 as the suction poppet 28 moves within the passageway 24. While it is desirable that the lip seal 42 is flexible enough to move smoothly into contact with portions of the suction poppet 28 during operation of the pump, it should also be rigid enough to provide a fluid-tight seal with the suction poppet 28 that will not allow pressurized fluid to move past these contact surfaces.

Pump body 12 further includes a fluid bypass chamber 46 that is connected for fluid communication with the fluid passageway 24 through a bypass input channel 62 and a bypass output channel 64. Bypass chamber 46 includes a ball check valve 54 that includes a ball 56 and a spring 58 that biases the ball toward a ball valve seat 52 when the valve is in its normal or equilibrium state. The ball check valve 54 can be opened by the force of pressurized fluid entering the fluid bypass chamber 46 through the bypass input channel 62 and forcing the ball 56 against the bias of the spring 58 so that fluid can exit the bypass chamber 46 through the bypass output channel 64. Notably, pressurized fluid that enters the bypass chamber 46 via the bypass output channel 64 will not open the ball check valve 54. Rather, such fluid will be prevented from moving through the bypass chamber 46 by the closed ball check valve 54, and will in fact increase the pressure of the ball 56 against the ball check valve 54.

FIG. 6 illustrates the pump assembly 70 with its components in a configuration that may be referred to as an auto-inflation resistance mode in which the cylinders are in a deflated condition and the reservoir 72 is in its filled or expanded condition. This condition is essentially the condition in which the pump assembly 70 will be configured until the user desires to inflate the cylinders. In this mode, the suction poppet 28 is being held against the bias of the suction poppet spring 32 by the flange 44 within the fluid passageway 24. An end 50 of suction poppet 28 is engaged with a nose portion 48 of poppet 36, thereby pushing the poppet 36 against the bias of poppet spring 38. The suction poppet 28 is positioned so that its outer surface is in contact with the lip seal 42, thereby creating a fluid-tight seal between the suction poppet 28 and the lip seal 42 to prevent movement of fluid into the tube 20 and attached cylinders. The pressurized fluid in the reservoir 72 will move into the transfer chamber 22, which can then move the suction poppet 28 slightly to the left against the bias of the suction poppet spring 32. Fluid can then flow from the transfer chamber 22 into the fluid passageway 24, then into the internal pump chamber 16. Movement of fluid into the pump chamber 16 will stop when the pressure has generally equalized between the pump bulb 14 and the reservoir 72. The face seal portion 30 will then move back into contact with the suction poppet valve seat 34, thereby limiting or preventing further fluid flow into the pump bulb 14 and placing the pump assembly 70 in a state of equilibrium.

As described above, any fluid moving into the fluid bypass chamber 46 through the bypass output channel 64 will be stopped by the ball check valve 54, thereby preventing fluid flow into the fluid passageway 24 or the tubes 20 by this path. When the pump assembly 70 reaches this state of equilibrium, fluid will then be held within the reservoir 72, the transfer chamber 22, and the internal pump chamber 16. While there may be small amounts of residual fluid within the cylinders, it is understood that the cylinders are preferably in their completely deflated or flaccid condition when the pump assembly 70 is configured in this mode.

To activate the pump assembly 70 to begin the cylinder inflation process, the user squeezes the pump bulb 14, which forces fluid contained within the internal pump chamber 16 through the connecting channel 26 and into fluid passageway 24. The high pressure of this fluid forces the face seal portion 30 of the suction poppet 28 past the flange 44, while the bias of the suction poppet spring 32 will push the face seal portion 30 against its valve seal 34 to provide a fluid-tight seal. Due to the contours of the suction poppet 28, the lip seal 42 will not be in contact with the suction poppet 28 at this point and fluid can thus move toward poppet 36. In this mode, the pressure of the fluid may be sufficient to also overcome the bias of the poppet spring 38 and break the fluid-tight contact between the poppet 36 and the poppet valve seat 40. When this occurs, fluid from the pump bulb 14 can continue past the poppet 36 and into tube 20. However, even if such fluid moves into tube 20, it will typically not be enough fluid to adequately inflate the cylinders. In order to achieve further cylinder inflation, the pump bulb 14 is then released, thereby allowing it to expand generally back to its original shape and size and placing the pump bulb chamber 16 and fluid passageway 24 under negative pressure. This negative pressure will cause the fluid to be drawn from the reservoir 72 through the reservoir channel 74, and into the pump bulb 14. Once this negative pressure is overcome through the movement of fluid into the pump bulb 14, the suction poppet spring 32 causes the suction poppet 28 to reseat itself against valve seat 34. The user may then squeeze the pump bulb 14 again to move the fluid from the internal pump chamber 16 to the cylinders, as described above relative to the pump activation step. This sequence of filling the pump bulb 14 under negative pressure and forcing the fluid from the pump bulb 14 under positive pressure may be repeated as many times as necessary to active the desired inflation of the cylinders and/or to empty the connected reservoir 72. However, due to stored energy of pressurized fluid in the reservoir 72, the fluid can transfer relatively quickly from the reservoir 72 to the pump bulb 14.

FIG. 7 illustrates the pump assembly 70 of FIG. 6 in the mode where enough fluid has been moved from the reservoir 72 that it is in a collapsed state. The fluid that was contained within the reservoir 72 has thus been transferred to the cylinders through the tube 20. In this mode, the bias of the poppet spring 38 and pressure of the fluid within the cylinders and connecting tube 20 are preferably sufficient to create a fluid-tight seal between the poppet 36 and the poppet valve seat 40. In this way, fluid cannot transfer from the cylinders into the fluid passageway 24, thereby keeping the cylinders inflated.

Referring also to FIG. 6, the cylinders can be deflated (and reservoir 72 filled or expanded) by manually compressing the walls of the pump body 12 in the area of the fluid passageway 24, which forces suction poppet 28 away from the suction poppet valve seat 34. When the suction poppet 28 is moved a sufficient distance, it will move past the flange 44, which will engage the face seal portion 30 to hold the suction poppet 28 away from the suction poppet spring 32. The seal between the poppet 36 and the poppet valve seat 40 is also broken by the movement of the suction poppet 28 into contact with the poppet 36 against the bias of the poppet spring 38. Fluid from the cylinders can then flow around the poppet 36, past the poppet valve seat 40, and into the fluid bypass chamber 46. Because this fluid is under pressure, it can open the ball check valve 54 and flow through the chamber 46, channel 64, fluid passageway 24, and then into the transfer chamber 22. The pressurized fluid will then move into the reservoir 72 until the pressure of the fluid in the reservoir 72 and pressure of the fluid in the cylinders have reached an equilibrium pressure. The cylinders may then be manually compressed or manipulated to transfer the remaining fluid in the cylinders to the reservoir 72. The reservoir membrane will then preferably be stretched to store energy within the reservoir 72. Thus, after the original compression of the pump body 12, the user does not need to further manipulate the pump body for fluid transfer from the cylinders.

Figure 8:
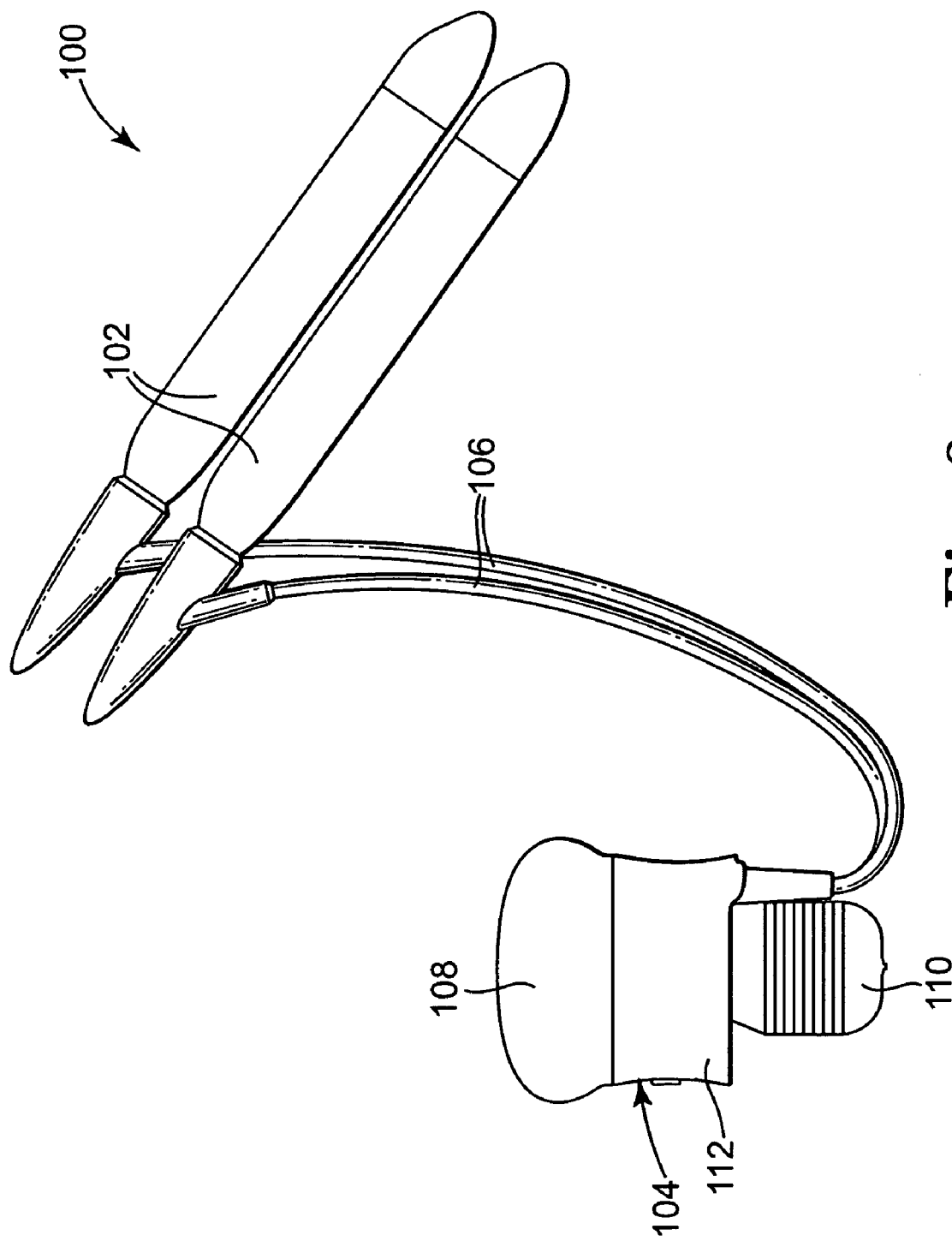
FIG. 8 is a schematic perspective view of an implantable penile prosthesis device having a pump and reservoir of the type illustrated in FIGS. 6 and 7, with the reservoir in its charged or filled condition.
Figure 9:
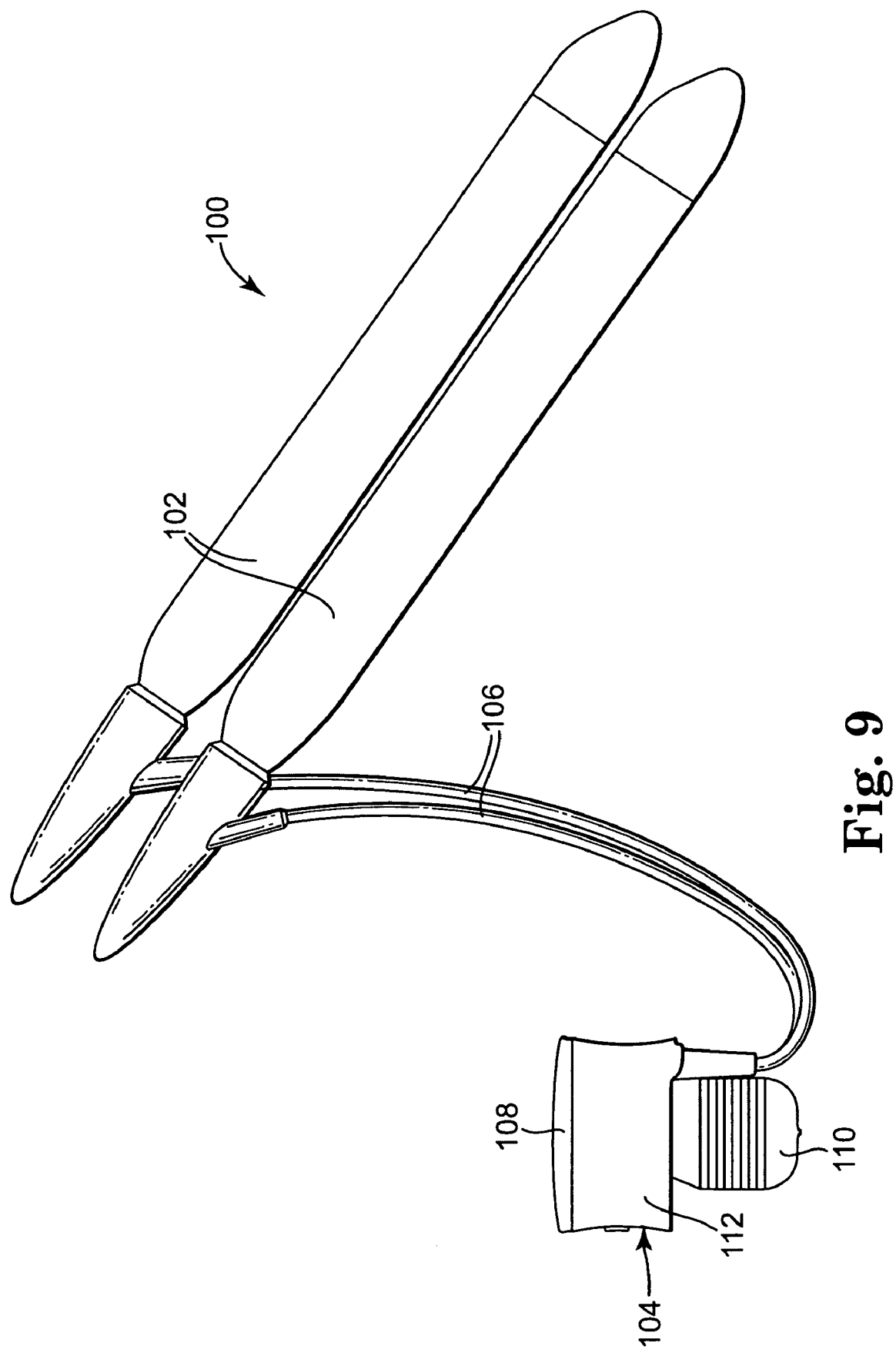
FIG. 9 is a schematic perspective view of the implantable penile prosthesis device of FIG. 8, with the reservoir in its discharged or collapsed condition.

Referring now to FIGS. 8 and 9, an implantable and inflatable two-piece penile prosthesis system 100 utilizing a pump assembly of the type described relative to FIGS. 6 and 7 is illustrated. Prosthesis system 100 generally includes a pair of cylinders 102 fluidly connected to a pump and reservoir assembly 104 by a pair of tubes 106. FIG. 8 illustrates the assembly 104 with a reservoir 108 in its filled or pressurized condition. In accordance with the present invention, when the reservoir 108 is filled or partially filled with fluid, the reservoir membrane will be stretched in such a way that the fluid within the reservoir 108 is under pressure and the reservoir 108 acts as an energy-storage device or capacitor. To activate the device and inflate the cylinders 102, the user activates the pump assembly 102 by squeezing the pump bulb 110, which causes the fluid in the pump bulb 110 to move through a pump body 112 and enter the cylinders 102. The fluid will continue to move from the reservoir 108 and into the cylinders 102 until the fluid from the pump bulb 110 is transferred from its internal chamber. At this point, the cylinders 102 will be partially filled. The user may then repeatedly squeeze the pump bulb 110 to transfer more fluid from the reservoir 108 to the cylinders 102 until the cylinders 102 reach a desired firmness or rigidity. This inflated condition or state of the cylinders 102 is shown generally in FIG. 9.

The system 100 is shown in FIG. 9 with the reservoir 108 being deflated or collapsed, while the cylinders 102 are in their inflated or rigid condition. Alternatively, the user may squeeze the reservoir 108 itself (after the initial activation of the pump body by squeezing) to cause the fluid to transfer and further inflate the cylinders 102. Because the energy of the pressurized fluid from the pump bulb 110 can cause a significant portion of the fluid to transfer with the initial activation step, the final pumping of the pump bulb 110 and/or reservoir 108 can involve as little as one or two squeezes to obtain rigidity.

In order to deflate the cylinders 102, the user will reactivate the pump by squeezing the ends of the pump body once, which will begin the initial transfer of fluid from the cylinders 102 into the reservoir 108 through a bypass chamber (not visible) within the pump body 112. This fluid will continue to flow toward the reservoir 108 until the pressure in the cylinders 102 and the pressure in the reservoir 108 are again in equilibrium. The user may then bend or squeeze the cylinders 102 to transfer the remainder of fluid back to the reservoir 108, thereby restoring flaccidity to the cylinders 102 and charging or filling the reservoir 108. No further interaction with the pump is necessary for this final fluid transfer. At this point, the reservoir 108 will again be storing fluid under pressure within its reservoir membrane and acting as an energy-storage device or capacitor for future activation of the system. Advantageously, the pump assembly 104 also includes an auto-inflation resistance feature, as described above, that is particularly beneficial when fluid is under pressure in the reservoir 108 to keep fluid from unintentionally moving into the cylinders 102. In this mode, a lip seal engages a suction poppet and prevents fluid flow from the reservoir 108 to the cylinders 102. In addition, a ball check valve in the bypass chamber will be closed, thereby preventing fluid flow to the cylinders 102 and resisting spontaneous inflation. Thus, the system of the present invention acts as an energy transfer system, where the particular valves, passageways, and chambers can be chosen from a wide variety of configurations and components, with the cylinders 102 and reservoir 108 alternately acting as the energy storage component of the system.

As described above, the cylinders can be partially inflated or partially deflated with a single squeezing motion that activates the system. This squeezing motion initiates the movement of pressurized fluid, which can be a significant portion of the total volume of fluid that needs to be transferred from the cylinders to the reservoir. Because a significant portion of the total fluid transfer occurs through this single squeezing motion, the system advantageously requires less manipulation, such as pumping or other motions, to move the fluid from the cylinders. Thus, this system can be completely activated in less time than other systems that require more dexterity, more repetitive motions, more complicated manipulations, and the like.

The systems of the present invention can utilize any inflatable and implantable cylinders that inflate and collapse as generally described for the pump and reservoir systems of this invention. Thus, the cylinders may be shaped and connected to the tubing generally as shown in the figures, but may instead have a different shape or contours, and may attach to the tubing in a different manner than that shown. However, in one preferred embodiment of the present invention, the cylinders are of a type having a non-expanding fabric. Preferably, the cylinders comprise parylene coated silicone inner and outer tubes. The cylinders may alternatively be of a type that includes an expanding fabric, if desired. Further, it is preferable that the entire device be adapted to include an antimicrobial treatment by providing a fluid-filling port, valve, or septum, such as that illustrated as filling port 76 in FIG. 6 and 7, so that it can be filled in the operating room.

Figure 10:
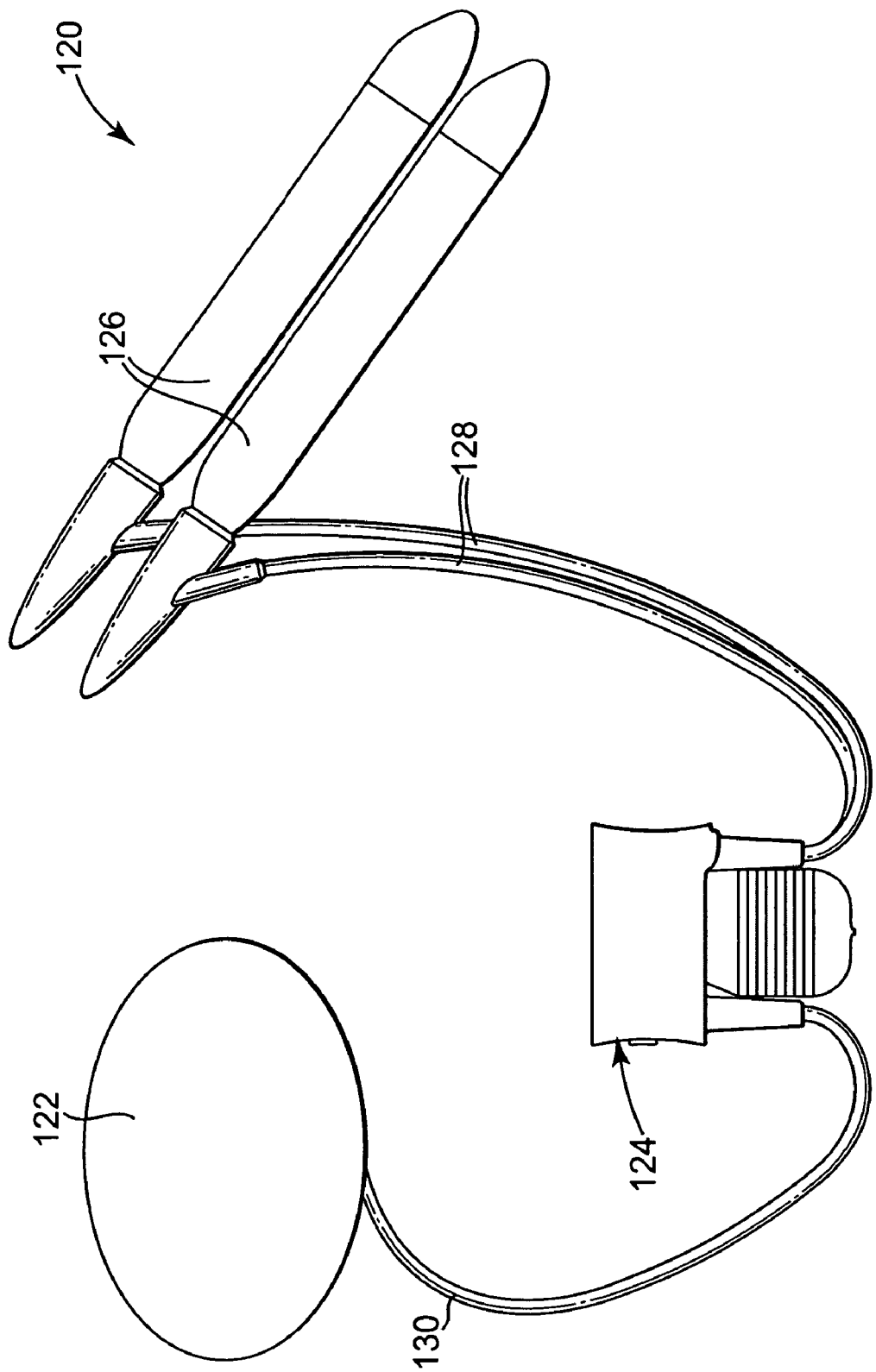
FIG. 10 illustrates a schematic perspective view of an implantable penile prosthesis device having a pump assembly of the type illustrated in FIGS. 1 through 5, with the reservoir in its filled condition.

FIG. 10 illustrates an embodiment of an implantable penile prosthesis system 120 of the present invention, which includes a pump of the type illustrated in FIGS. 1 through 5, a reservoir 122 that is separate from a pump assembly 124, and cylinders 126. In general, this system 120 utilizes a pump assembly 124 and a reservoir 122 to inflate the cylinders 126, with connecting tubing attached between the pump assembly 124 and both the reservoir 122 and the cylinders 126. The pump assembly 124 can also be used to deflate the cylinders, as described above. The reservoir 122 is preferably constructed from a thick, high durometer elastomeric material, such as silicone and is specifically sized to hold a certain volume of fluid that corresponds to the volume difference desired to expand the cylinders 126. The reservoir 122 is preferably designed so that the internal pressure of the reservoir 122 increases as it is filled with liquid, until a relatively constant pressure is achieved.

As shown, two tubes 128 extend from the pump assembly 124, each of which connects to one of the cylinders 126. A single tube 130 extends from the reservoir 122 for connection to the pump 124. It is understood, however, that the number of tubes and the branching of tubes can differ from this arrangement, depending on the design of the pump and other components. As described above relative to the pump assemblies 10 and 70, the body of the pump assembly 124 can be squeezed generally along its longitudinal axis in order to deflate the cylinders 126, which thereby opens certain valves within the pump and allows pressurized fluid from the cylinders to move through the pump and enter the reservoir. Inflation of the cylinders can be accomplished by first squeezing the pump bulb to activate the pump assembly 124, then squeezing the pump bulb repeatedly until the desired cylinder inflation is achieved In the embodiments described above, the reservoir is preferably made of an elastic material that expands with the transfer of fluid to the reservoir, thereby pressurizing the fluid and causing the reservoir to act as an energy-storing device or capacitor. While the use of a pressurized fluid in the embodiments of the present invention describe several exemplary embodiments, it is understood that the concepts of pressurizing fluid in these types of systems is adaptable to systems with various types of pumps, cylinders, and reservoirs that provide the same features as those described relative to the present invention.

The present invention has now been described with reference to several embodiments thereof. The entire disclosure of any patent or patent application identified herein is hereby incorporated by reference. The foregoing detailed description and examples have been given for clarity of understanding only. No unnecessary limitations are to be understood therefrom. It will be apparent to those skilled in the art that many changes can be made in the embodiments described without departing from the scope of the invention. Thus, the scope of the present invention should not be limited to the structures described herein, but only by the structures described by the language of the claims and the equivalents of those structures.

What is claimed is:

1. A penile prosthesis comprising:
    at least one cylinder;
    a reservoir; and
    a pump for transferring fluid between the reservoir and the at least one cylinder, the pump comprising:
        a pump housing;
        at least one reservoir channel fluidly coupling the pump housing to the reservoir;
        at least one cylinder tube fluidly connecting the pump housing to the at least one cylinder;
        a fluid passageway fluidly coupled to the at least one cylinder tube and a transfer chamber and comprising a flange extending toward its interior, wherein the transfer chamber is fluidly coupled to the reservoir channel;
        a first poppet biased toward a first valve seat within the fluid passageway and comprising an elongated body having an extending face seal portion for engagement with the flange of the fluid passageway when the first poppet is displaced by a sufficient distance from the first valve seat;
        a second poppet biased toward a second valve seat, biased away from the first valve seat, and generally in alignment with the first poppet within the fluid passageway, wherein the fluid passageway further comprises a lip seal portion that extends generally from the second poppet toward the first poppet, wherein the first poppet is slideably moveable into contact with the lip seal to prevent fluid from moving between the pump bulb and the fluid passageway adjacent the second poppet;
        a bypass chamber fluidly connected by a bypass input channel to the fluid passageway at a first location that is located on a side of the lip seal adjacent the second poppet and fluidly connected by a bypass output channel to the fluid passageway at a second location that is located on a side of the lip seal that is further from the second poppet than the bypass input channel, the bypass chamber comprising a bypass check valve biased toward a closed position; and
        a pump bulb fluidly connected to the fluid passageway between the bypass input channel and bypass output channel along the length of the fluid passageway;
        wherein the pump has a deflation mode in which compression of a portion of the pump body moves the first poppet into sealing contact with the lip seal portion and the second poppet to unseat the second poppet from the second valve seat to provide a gap between the second poppet and the second valve seat for pressurized fluid to flow from the at least one cylinder past the second poppet and into the bypass chamber through the bypass input channel.

2. The prosthesis of claim 1, further comprising a cylinder inflation mode in which the face seal portion of the first poppet is seated against the first valve seat, the lip seal portion is spaced from the first poppet, and the pump bulb is compressible for forcing enough fluid under pressure from the pump bulb into the fluid passageway to unseat the second poppet from the second valve seat and allow fluid to move past the second poppet and enter the at least one cylinder tube.

3. The prosthesis of claim 1, further comprising a pump bulb filling mode in which the lip seal portion is in contact with the first poppet and the pump bulb is expandable to place the fluid passageway and transfer chamber under negative pressure to thereby unseat the face seal portion of the first poppet from the first valve seat against the bias of a first poppet spring and draw fluid into the pump bulb.

4. The prosthesis of claim 1, wherein the at least one cylinder is expandable in response to movement of pressurized fluid from the reservoir through the pump and into the at least one cylinder, thereby pressurizing the fluid within the at least one cylinder.

5. The prosthesis of claim 1, wherein a fluid pressure level of fluid flowing from the at least one cylinder into the bypass chamber is sufficient to unseat the ball from the ball valve seat and allow fluid to flow through the bypass output channel and into the transfer chamber of the pump housing.

6. The prosthesis of claim 1, wherein the ball check valve is not openable by a flow of pressurized fluid from the fluid passageway into the bypass output channel.

7. The prosthesis of claim 1, wherein the first poppet remains in contact with the second poppet and the second poppet remains unseated from the second valve seat when the pump body is not under compression.

8. The prosthesis of claim 1, wherein the reservoir is fluidly connected to the reservoir channel by at least one reservoir tube.

9. The prosthesis of claim 1, wherein the pump housing is partially compressible generally along an axis that runs longitudinally through the fluid passageway so that a compression of the pump housing at generally opposite ends of the fluid passageway will displace at least one of the first and second poppets.

10. The prosthesis of claim 1, wherein the reservoir channel is an opening extending from the transfer chamber through the pump housing for fluidly connecting the transfer chamber to the reservoir.

11. The prosthesis of claim 1, wherein the reservoir comprises an outer reservoir membrane surrounding at least a portion of an internal reservoir chamber, wherein the reservoir chamber can expand from a first internal volume to a second internal volume that is larger than the first internal volume by the addition of pressurized fluid.

12. The prosthesis of claim 11, wherein the pump housing comprises a lower face surface and wherein the reservoir chamber is defined by the reservoir membrane and at least a portion of the lower face surface of the pump housing.

13. The prosthesis of claim 12, wherein the lower face surface is resistant to deformation by the pressure of fluid being held within the reservoir chamber.

14. The prosthesis of claim 12, wherein the reservoir membrane can expand when a volume of fluid entering the reservoir chamber is greater than a first internal volume of the reservoir chamber.

15. The prosthesis of claim 12, wherein the reservoir functions as an energy-storing device when a volume of pressurized fluid in the reservoir chamber forces the reservoir membrane to expand.

16. The prosthesis of claim 1 wherein the bypass check valve comprises a ball biased toward a ball valve seat within the bypass chamber.

17. The prosthesis of claim 1, wherein the lip seal portion is annular.

18. The prosthesis of claim 1, further comprising a filling port fluidly connected to the transfer chamber for adding a predetermined volume of fluid to the prosthesis.

19. A pump for transferring fluid between a reservoir and at least one cylinder within a penile prosthesis, the pump comprising:

a pump housing;

at least one reservoir channel fluidly coupling the pump housing to the reservoir;

at least one cylinder tube fluidly connecting the pump housing to the at least one cylinder;

a fluid passageway fluidly coupled to the at least one cylinder tube and a transfer chamber and comprising a flange extending toward its interior, wherein the transfer chamber is fluidly coupled to the reservoir channel;

a first poppet biased toward a first valve seat within the fluid passageway and comprising an elongated body having an extending face seal portion for engagement with the flange of the fluid passageway when the first poppet is displaced by a sufficient distance from the first valve seat;

a second poppet biased toward a second valve seat, biased away from the first valve seat, and generally in alignment with the first poppet within the fluid passageway, wherein the fluid passageway further comprises a lip seal portion that extends generally from the second poppet toward the first poppet, wherein the first poppet is slideably moveable into contact with the lip seal to prevent fluid from moving between the pump bulb and the fluid passageway adjacent the second poppet;

a bypass chamber fluidly connected by a bypass input channel to the fluid passageway at a first location that is located on a side of the lip seal adjacent the second poppet and fluidly connected by a bypass output channel to the fluid passageway at a second location that is located on a side of the lip seal that is further from the second poppet than the bypass input channel, the bypass chamber comprising a bypass check valve biased toward a closed position; and a pump bulb fluidly connected to the fluid passageway between the bypass input channel and bypass output channel along the length of the fluid passageway;

wherein the pump has a deflation mode in which compression of a portion of the pump body moves the first poppet into sealing contact with the lip seal portion and the second Poppet to unseat the second poppet from the second valve seat to provide a gap between the second poppet and the second valve seat for pressurized fluid to flow from the at least one cylinder past the second poppet and into the bypass chamber through the bypass input channel.

* * * * *